US00PP29340P2

(12) United States Plant Patent
Danziger

(10) Patent No.: US PP29,340 P2
(45) Date of Patent: May 29, 2018

(54) ***PETUNIA* 'DPECAPBURG'**

(50) Latin Name: *Petunia hybrida*
Varietal Denomination: DPECAPBURG

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 0 days. days.

(21) Appl. No.: 15/731,011

(22) Filed: Apr. 7, 2017

(51) Int. Cl.
*A01H 5/02* (2018.01)

(52) U.S. Cl.
USPC ..... Plt./356.18

(58) Field of Classification Search
USPC ..... Plt./356.18
See application file for complete search history.

*Primary Examiner* — Annette H Para
(74) *Attorney, Agent, or Firm* — Cassandra Bright

(57) ABSTRACT

A new and distinct *Petunia* cultivar named 'DPECAPBURG' is disclosed, characterized by well-branched plants with a semi-trailing growth habit, abundant flowering and medium vigor. Flower color is purple with a blue throat, flowers are large. The new variety is a *Petunia*, normally produced as an outdoor garden or container plant.

2 Drawing Sheets

Figure 1:
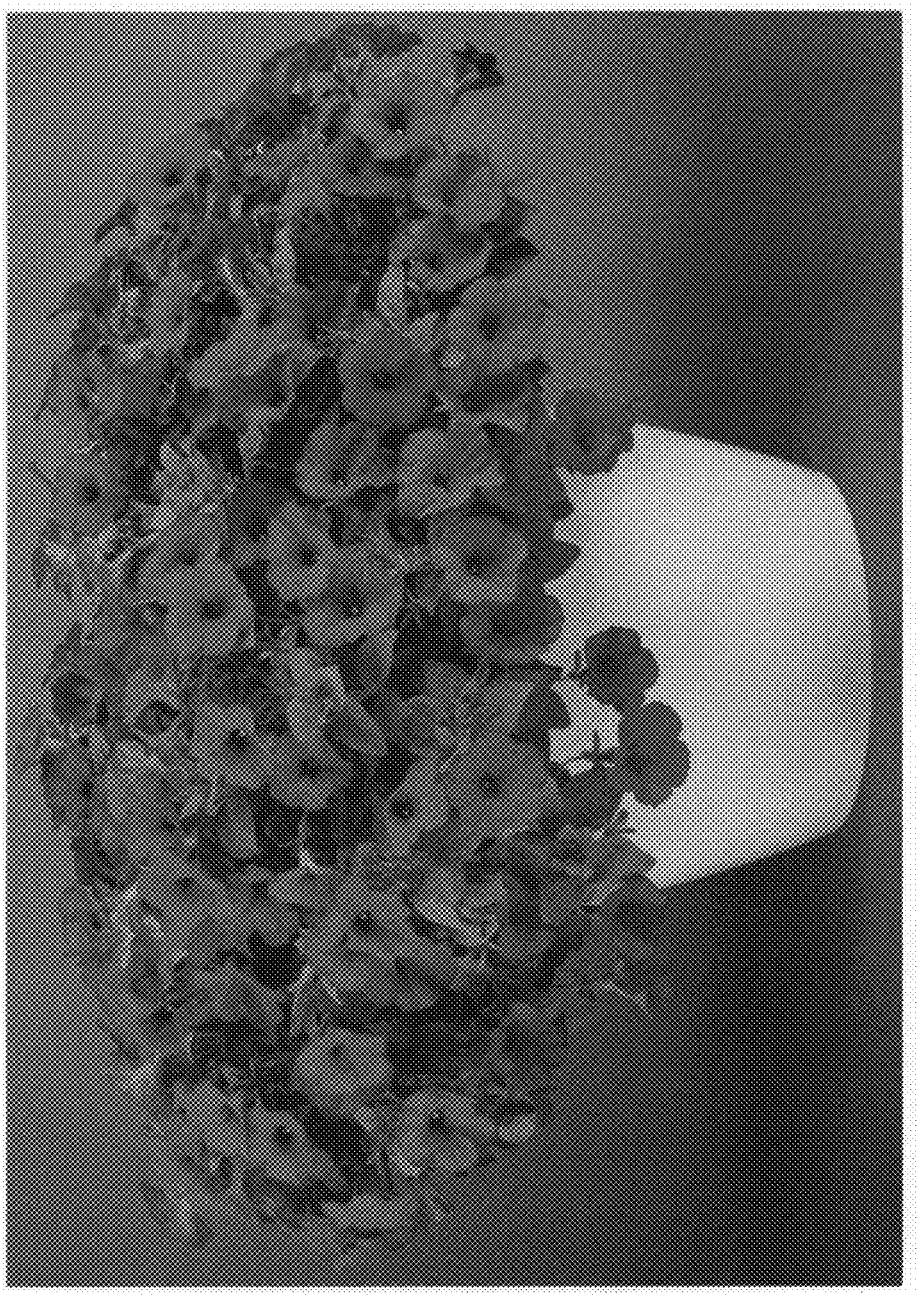

Latin name of the genus and species: *Petunia hybrida.*
Variety denomination: 'DPECAPBURG'.

BACKGROUND OF THE INVENTION

The new *Petunia hybrida* cultivar is a product of a planned breeding program conducted by the inventor, Gavriel Danziger in Moshav Mishmar Hashiva, Israel. The objective of the breeding program was to produce new *Petunia* varieties with large flower and abundant flowering. The cross resulting in this new variety was made during October of 2013.

The seed parent is the unpatented, propriety variety referred to as *Petunia* 'cv. 13-7184'. The pollen parent is the unpatented, propriety variety referred to as *Petunia* 'cv. 13-7567'. The new variety was discovered in July of 2014 by the inventor in a group of seedlings resulting from the 2013 crossing, in a greenhouse in Moshav Mishmar Hashiva, Israel.

Asexual reproduction of the new cultivar 'DPECAPBURG' was first performed by terminal vegetative cuttings during July of 2014, at a greenhouse in Moshav Mishmar Hashiva, Israel. Subsequent propagation by has shown that the unique features of this cultivar are stable and reproduced true to type in more than 25 successive generations.

SUMMARY OF THE INVENTION

The cultivar 'DPECAPBURG' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DPECAPBURG' These characteristics in combination distinguish 'DPECAPBURG' as a new and distinct *Petunia* cultivar:

1. Semi-trailing growth habit.
2. Very well-branched plants with medium vigor.

3. Flowers color is purple with a blue throat.
4. Large flower size.
5. Abundant flowering.

PARENT COMPARISON

Plants of the new cultivar 'DPECAPBURG' are similar to plants of the seed parent, *Petunia* 'cv. 13-7184' in most horticultural characteristics, however, plants of the new cultivar 'DPECAPBURG' differ in the following:

1. The new variety is semi-trailing, the seed parent plant habit is more upright.
2. The new variety is more vigorous and less compact.
3. Seed parent flower color is white with black stripes, compared to purple with a blue throat.
4. Flower size of the seed parent is medium, flower size of the new variety is large.
5. The new variety flowers more abundantly.

Plants of the new cultivar 'DPECAPBURG' are similar to plants of the pollen parent, *Petunia* 'cv. 13-7567' in most horticultural characteristics however, plants of the new cultivar 'DPECAPBURG' differ in the following:

1. The pollen parent has a trailing growth habit, the new variety is semi-trailing.
2. Vigorous, branched plant.
3. Flower color of the pollen parent is magenta, the new variety is purple with a blue throat.
4. Flowers of the pollen parent are extra large, flowers of the new variety large.
5. The new variety flowers more abundantly.

COMMERCIAL COMPARISON

Plants of the new cultivar 'DPECAPBURG' can be compared to the unpatented commercial variety *Petunia hybrida* 'Purple Vein Ray'. These varieties are similar in most horticultural characteristics; however, 'DPECAPBURG' differs in the following:

1. Comparator flower color is Violet-Purple with purple veins, while the new variety has Purple flowers.

2. Comparator flower shape is rounded, while the flower of the new variety is more star-shaped.
3. Comparator plant is taller than the new variety.

Plants of the new cultivar 'DPECAPBURG' can also be compared to the unpatented commercial variety *Petunia hybrida* 'Purple Ray'. These varieties are similar in most horticultural characteristics; however, 'DPECAPBURG' differs in the following:

1. Comparator flower size is larger than the flower of the new variety.
2. Comparator plant is more vigorous than the new variety.
3. Comparator plant is taller than the new variety.

BRIEF DESCRIPTION OF THE PHOTOGRAPHS

The accompanying photograph in FIG. 1 illustrates in full color a typical plant of 'DPECAPBURG' grown in a greenhouse, in Moshav Mishmar Hashiva, Israel.

Figure 2:
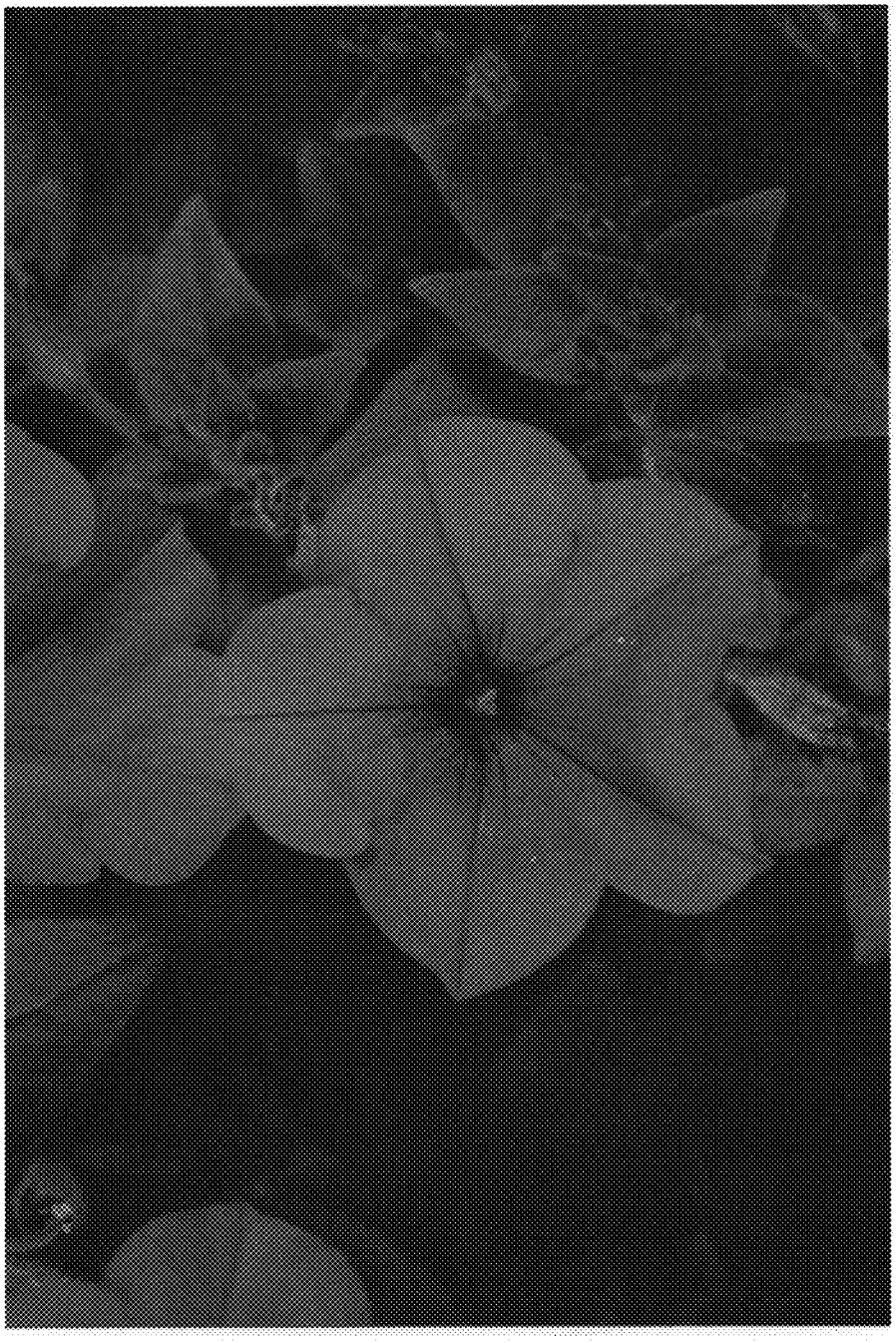

FIG. 2 illustrates in full color a typical mature flower of 'DPECAPBURG' during Spring. Age of the plant photographed is approximately 90 days from a rooted cutting in a 13 cm pot.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DPECAPBURG' plants grown in greenhouse in Moshav Mishmar Hashiva, Israel, under natural lighting. Measurements were taken during April of 2015. The plants were approximately 60 days from a rooted cutting in a 13 cm pot. The growing temperature ranged from 20° C. to 35° C. during the days, 17° C. to 23° C. during the nights. Measurements and numerical values represent averages of typical plant types.

Botanical classification: *Petunia hybrida* 'DPECAPBURG'.

PROPAGATION

Time to initiate roots: 10-14 days at approximately 20° C.

PLANT

Growth habit: Semi-Trailing.
Pot size of plant described: 13 cm.
Height: To top of flowers: about 15 cm.
Plant spread: About 50 cm.
Growth rate: Medium.
Branching characteristics: Very well branched.
Length of primary lateral branches: About 25 cm.
Diameter of lateral branches: About 0.4 cm.
Quantity of primary lateral branches: 8.
Characteristics of primary lateral branches:
- *Form*.—Cylindrical.
- *Diameter*.—About 0.4 cm.
- *Color*.—RHS Yellow-Green 144 B.
- *Texture*.—Pubescent.
- *Strength*.—Good.

Internode length: About 1.2 cm.

FOLIAGE

Leaf:
- *Arrangement*.—Opposite.
- *Quantity*.—Approximately 30 per branch.
- *Average length*.—4.5 cm.
- *Average width*.—2.0 cm.
- *Shape of blade*.—Elliptic.
- *Apex*.—Acute.
- *Base*.—Acute.
- *Margin*.—Entire.
- *Texture of top surface*.—Velvety.
- *Texture of bottom surface*.—Velvety.
- *Color*.—Young foliage upper side: RHS Green 137 A. Young foliage under side: RHS Green 137 B. Mature foliage upper side: RHS Green 137 A. Mature foliage under side: RHS Green 137 B.
- *Venation*.—Type: Pinnate. Venation color upper side: RHS Green 137 B. Venation color under side: RHS Green 137 C.
- *Petiole*.—Length: About 0.3 cm. Diameter: About 0.2 cm. Color: RHS Green 137 A.
- Texture: Velvety

FLOWER

Natural flowering season: Spring, Summer and Autumn in Beit Dagan, Israel.
Days to flowering from rooted cutting: About 30 days.
Inflorescence and flower type and habit: Axillary, single flower, salver form shape, erect habit.
Rate of flower opening: 2 to 3 days from bud to fully opened flower.
Flower longevity on plant: 3 to 6 days.
Approximate quantity of flowers per plant: About 70.
Persistent or self-cleaning: Self-cleaning.
Bud:
- *Shape*.—Tubular.
- *Length*.—About 4.5 cm.
- *Diameter*.—About 0.7 cm.
- *Color*.—RHS Purple 79 C.

Flower size:
- *Diameter*.—About 5.5 cm.
- *Flower tube length*.—About 3 cm.
- *Flower tube diameter at distal end*.—1.5 cm.
- *Flower tube diameter at proximal end*.—0.3 cm.

Petals:
- *Length from throat*.—About 2.3 cm.
- *Width*.—About 2.8 cm.
- *Quantity*.—5.
- *Texture*.—Velvety.
- *Apex*.—Blunt.
- *Margin*.—Entire.

Color:
- *When opening*.—Upper surface: RHS Purple N 79 B. Lower surface: RHS Purple N 79 D.
- *Fully opened*.—Upper surface: RHS between Purple N 78 A and Red-Purple N 74 A. Lower surface: Purple N 78 B. Flower throat (inside): RHS Violet-Blue N 89 A. Flower throat, vein: RHS Violet-Blue N 89 A. Flower tube (outside): RHS Purple 79 C. Flower tube, vein: RHS Purple 79 A.
- *Fading*.—Petals fading to: RHS Violet 83 A.

Calyx/sepals:
*Quantity per flower.*—5.
*Shape*.—Linear.
*Length*.—About 1.4 cm.
*Width*.—About 0.3 cm.
*Apex*.—Acute.
*Base*.—Cuneate.
*Margin*.—Entire.
*Texture*.—Velvety all surfaces.
*Color*.—Upper Surface: RHS Green 137 A. Lower Surface: RHS Green 137 B.

Pedicel:
*Length*.—About 2.5 cm.
*Diameter*.—About 0.2 cm.
*Color*.—RHS Yellow-Green 144 B.
*Orientation*.—45 degrees from center of stem.

Peduncle: Not present.

Fragrance: None.

REPRODUCTIVE ORGANS

Stamens:
*Number*.—5.
*Filament length*.—About 1.8 cm.

Anthers:
*Length*.—About 0.1 cm.
*Shape*.—Rounded.
*Color*.—RHS Yellow 5 D.
*Pollen*.—Color: RHS Yellow 5 D. Quantity: Abundant.

Pistil:
*Number*.—1.
*Length*.—About 3.0 cm.
*Style*.—Length: About 1.9 cm. Color: RHS Green-Yellow 1 C.
*Stigma*.—Shape: Rounded. Color: RHS Yellow-Green 144 C. Ovary Color: RHS Yellow-Green 144 B.

OTHER CHARACTERISTICS

Seeds and fruits: About 80 Brown, rounded seeds of about 0.5 mm diameter, per one brown, conical capsule. Colors not accurately measured with R.H.S. chart.

Disease/pest resistance: Neither resistance nor susceptibility to the normal diseases and pests of *Petunia* have been observed. Typical well known diseases include: *Botrytis cineria, Fusarium, Pythium, Phytophthora*, and *Rhizoctonia* species. Typical well known pests include: Leaf miners, spider mites, thrips and possibly caterpillars.

Temperature tolerance: Tolerates a range between 5° C. to 40° C.

What is claimed is:

1. A new and distinct cultivar of *Petunia* plant named 'DPECAPBURG' as herein illustrated and described.

* * * * *